United States Patent [19]

Boquet

[11] Patent Number: 5,789,243

[45] Date of Patent: Aug. 4, 1998

[54] CARTRIDGE FOR PREPARING PURIFIED NUCLEIC ACIDS

[75] Inventor: Jean Boquet, Le Perray-en-Yvelines, France

[73] Assignee: Bertin & Cie, Plaisir, France

[21] Appl. No.: 637,713

[22] PCT Filed: Nov. 15, 1994

[86] PCT No.: PCT/FR94/01327

§ 371 Date: May 1, 1996

§ 102(e) Date: May 1, 1996

[87] PCT Pub. No.: WO95/14086

PCT Pub. Date: May 26, 1995

[30] Foreign Application Priority Data

Nov. 16, 1993 [FR] France ................... 93 13621

[51] Int. Cl.$^6$ ................... C12M 1/12; C12M 3/06
[52] U.S. Cl. ................... 435/306.1; 435/297.1; 435/270; 422/101; 210/321.64
[58] Field of Search ................... 435/6, 259, 283.1, 435/306.1, 297.2, 297.3, 297.1, 270; 536/25.4, 25.41; 210/321.64, 321.78, 321.87, 323.1, 342; 436/178; 422/101

[56] References Cited

U.S. PATENT DOCUMENTS

| 4,787,963 | 11/1988 | MacConnell. |
| 4,921,952 | 5/1990 | Longmire et al.. |
| 5,352,609 | 10/1994 | Boquet ................... 435/270 |

FOREIGN PATENT DOCUMENTS

| 245945 | 11/1987 | European Pat. Off. . |
| 431905 | 6/1991 | European Pat. Off. . |
| WO 90/15148 | 12/1990 | WIPO . |
| WO 93/01312 | 1/1993 | WIPO . |

Primary Examiner—William H. Beisner
Attorney, Agent, or Firm—Bell Seltzer Intellectual Property Law Group of Alston & Bird

[57] ABSTRACT

The invention relates to a cartridge for preparing purified nucleic acids obtained from a sample of cells, the cartridge comprises a filter tube disposed inside a dialysis tube, the ends of the tubes are mounted in endpieces that are interconnected by rigid uprights, the endpieces are designed to be connected to a device for injection and delivery of substances such as a sample of cells, reaction substances, and rinsing substances.

10 Claims, 3 Drawing Sheets

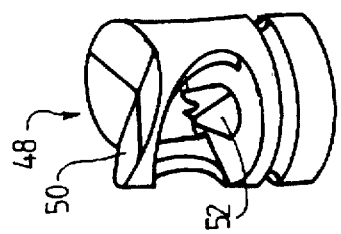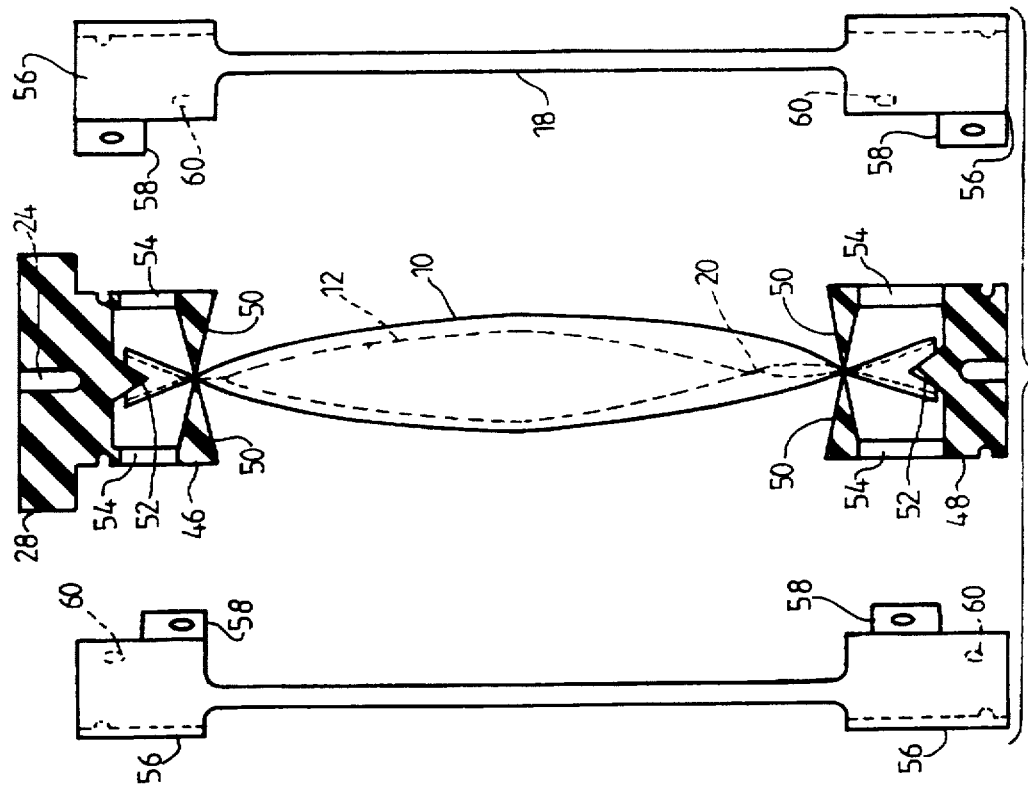

CARTRIDGE FOR PREPARING PURIFIED NUCLEIC ACIDS

FIELD AND BACKGROUND OF THE INVENTION

The invention relates to a cartridge for extracting and purifying nucleic acids, in particular genome DNA, from a blood sample, a tissue cell sample, or a culture cell sample.

International application WO 93/01312 has already disclosed a cartridge of this type constituting a considerable advance over competing devices by virtue of its ease of use, its efficiency, its reliability, and the economic conditions required for manufacturing and using it.

The cartridge described in that prior application comprises a flat frame having a dialysis membrane stuck to each of the two faces thereof, thereby defining a dialysis enclosure between them. A plane filter for retaining cell nuclei is mounted inside the frame between the membranes, and means are provided for causing the following to flow between the membranes: a sample of lysed cells; substances for washing and rinsing the nuclei retained by the filter; and substances for lysing the nuclei and degrading proteins. The nucleic acids released into the enclosure are purified by dialysis. For some cells, the operations of cell lysis, nucleus lysis, degradation of proteins and other contaminants, and dialysis can all be done directly in the enclosure.

The cartridge serves to automate the operations of extracting and purifying nucleic acids, which operations take place in the cartridge without it being manipulated.

SUMMARY OF THE INVENTION

The present invention seeks to improve that cartridge, aiming to simplify its structure and its manufacture, to reduce its cost, and to improve its operation, its performance, and its reliability.

To this end, the invention provides a cartridge for preparing purified nucleic acids, the cartridge comprising a dialysis enclosure, insertion means for inserting a sample of cells and reaction substances into said enclosure, discharge means for discharging reaction substances and purified nucleic acids, and a filter for retaining cell nuclei, the filter being disposed inside the dialysis enclosure, the cartridge being characterized in that the filter and the dialysis enclosure are constituted by a flexible filter tube and a flexible dialysis tube placed one within the other, the filter tube being open at one end and closed at the other, the dialysis tube being open at both ends, said ends being mounted together with at least the open end of the filter tube in endpieces of plastics material or of elastomer designed to receive the above-mentioned insertion and discharge means.

The flexible tubular structures of the filter and of the dialysis enclosure enable the system to be drained completely by suction, where the effect of the suction is to flatten the filter tube and the dialysis tube onto themselves so as to leave no residual internal volume. In addition, the dialysis enclosure contains no foreign body other than the filter tube, thereby reducing the risk of contamination or of pollution.

In a preferred embodiment of the invention, each endpiece includes a hollow body or cap of material that is self-sealing after being pierced, receiving an open end of the filter tube and/or of the dialysis tube, and embedded in a sealant.

The endpieces are also rigidly interconnected, e.g. by longitudinal uprights which are fixed by mutual engagement and/or adhesive to the endpieces.

In general, the cartridge of the invention is designed to be placed in a tube or a housing connected to means for circulating a dialysis liquid.

BRIEF DESCRIPTION OF THE DRAWINGS

The invention will be better understood and other characteristics, details, and advantages thereof will appear more clearly on reading the following description given by way of example and made with reference to the accompanying drawings, in which:

FIGS. 3 and 4 are diagrams of the filter tube and of the dialysis tube;

FIG. 5 is a diagram showing a step during the mounting of a cartridge of the invention;

FIG. 6 is a perspective diagram of an endpiece;

DESCRIPTION OF THE PREFERRED EMBODIMENTS

Figure 1:
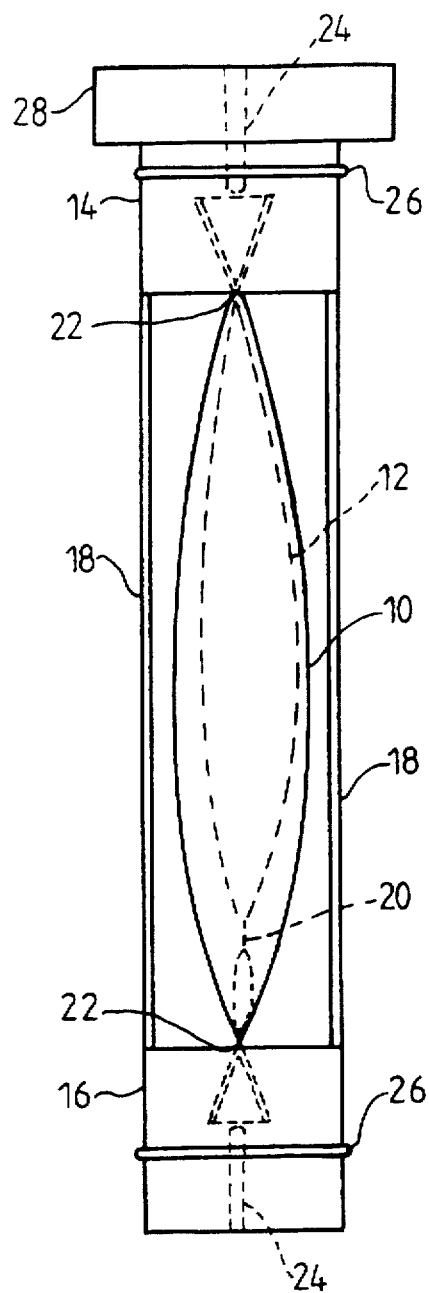
FIG. 1 is a diagram of a cartridge of the invention.

The cartridge of the invention as shown in FIG. 1 essentially comprises a flexible cylindrical dialysis tube 10 containing a flexible cylindrical filter tube 12, the filter tube being made of a microporous material having the property of retaining cell nuclei, plus endpieces 14 and 16 that are rigidly interconnected by uprights 18 outside the dialysis tube 10, and in which the ends of the dialysis tube 10 and of the filter tube 12 are mounted.

The dialysis tube 10 is open at both ends, while the filter tube 12 is open at its top end and is closed near its bottom end, e.g. by a sealing transverse weld line 20. Also, the dialysis tube 10 and the filter tube 12 are resiliently pinched and flattened in the vicinity of their ends where they penetrate into the endpieces 14 and 16, as shown at 22, with the ends proper of said tubes flaring thereafter inside the endpieces 14 and 16, as can be seen in the drawing.

Blind axial bores 24 are formed in the endpieces 14 and 16 from their outside ends and they extend towards the flared and open ends of the tubes 10 and 12.

At least one O-ring 26 is mounted for sealing purposes on the cylindrical surface of each endpiece, and the top endpiece 14 has an enlarged head 28.

Figure 2:
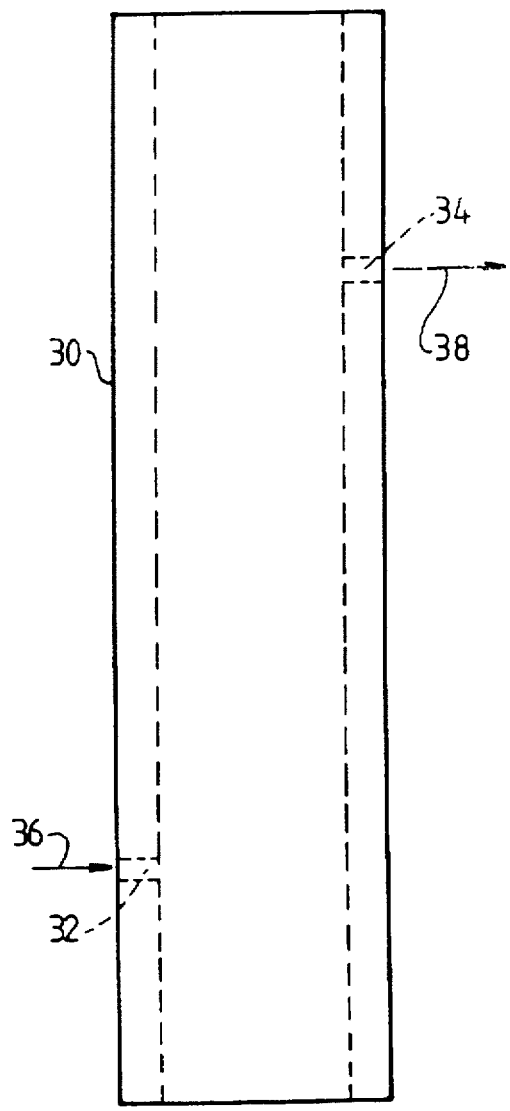
FIG. 2 is a diagram of a tube designed to receive the cartridge.

Such a cartridge is designed to be used inside a cylindrical tube or housing 30 as shown in FIG. 2, having an inside diameter that corresponds substantially to the outside diameter of the endpieces 14 and 16, or of their O-rings 26. Thus, the cartridge can be mounted in sealed manner inside the tube 30 by means of its endpieces 14 and 16 which close the top and bottom ends of the tube in sealed manner, the head 28 of endpiece 14 being pressed against the top end of the tube 30.

The tube has two radial ducts 32 and 34 at different heights and formed so as to open out to the inside of the tube 30 between the endpieces 14 and 16 of the cartridge, with these radial ducts being designed to be connected to liquid feed and discharge means 36 and 38 for dialysis purposes and to means for applying pressure or suction to the cartridge.

Reference is now made to FIGS. 3 to 6 to describe the structure and mounting of the cartridge of the invention in greater detail.

FIG. 3 shows the filter tube 12 which is constituted by a cylindrical film of microporous material suitable for retaining cell nuclei, with said microporous material being constituted, for example, by a polyester cloth having a thickness of about 0.1 millimeters and a pore size of about 1 micron. Such filter cloth is commercially available.

The tube 12 is closed in the vicinity of its bottom end by a sealing transverse weld line 20 and two openings 40 are formed in the tube immediately below said weld line. In addition, other holes 42 are also formed through the tube 12 in the immediate vicinity of its ends, for a role that is explained below.

FIG. 4 shows the dialysis tube 10 which is of substantially the same length as the filter tube 12 and of diameter slightly greater than that of the filter tube. The dialysis tube 10 is open at both ends, as mentioned above, and it includes holes 44 in the immediate vicinity of its ends, said holes 44 corresponding to the holes 42 of the filter tube 12.

By way of example, the dialysis tube 10 may be made of a nylon film having a thickness of about 0.1 millimeters and a pore size of about 0.1 μm.

By way of concrete example only, it is specified that the tubes 10 and 12 may be about 50 mm long, with the filter tubes 12 having a diameter of about 5 mm and the dialysis tube 10 having a diameter of about 6.5 mm.

The filter tube 12 is placed inside the dialysis tube 10 and the ends of these tubes are mounted in the endpieces 14 and 16 in the manner described below with reference to FIG. 5.

Each endpiece 14 and 16 essentially comprises a respective body 46 or 48 that is generally in the form of a hollow cylinder and made of an elastomer material of the type that is self-sealing after being punctured, such as a "bromobutyl". Each body 46, 48 is formed with the above-mentioned blind bore 24 and the top body 46 has the above-mentioned enlarged head 28.

The facing ends of these bodies include respective very narrow elongate slits for receiving the ends of the tubes 10 and 12, each slit being defined by two lips 50 that extend towards each other and that press against each other, so that the width of the resulting slit is substantially zero. The inside wall of each body remote from the slit may include a triangular section projection 52 directed towards the slit and engaged at least in part in the ends of the tubes 10 and 12 so as to open them out and cause them to flare slightly.

As can be seen more clearly in FIG. 6, the cylindrical wall of each body 46, 48 is constituted by arms extending between two large side openings 54, thereby imparting flexibility to the lips 50. The openings are closed subsequently by a sealant.

Each body 46, 48 is clamped in two semi-cylindrical shells 56, e.g. made of rigid plastics material integrally molded with the above-mentioned uprights 18 each of which connects a shell 56 for one endpiece to a shell 56 for the other endpiece. The two semi-cylindrical shells 56 for each endpiece are assembled together, e.g. by resilient snap-fastening means as shown at 58 and 60, and/or by means of O-rings 26 which are threaded over the shells and engage in annular grooves provided for that purpose. When the shells 56 are assembled together in this way, they enclose the bodies 46 and 48 like molds. It is then possible to insert a hollow needle into the bore 24 of each body 46, 48, to pass it through the end wall thereof, and to inject a sealant into each body, e.g. such as silicone which is relatively soft and which adheres well to the ends of the tubes 10 and 12 and to the walls of the bodies 46 or 48. The holes 42 and 44 formed in the immediate vicinity of the ends of the tubes 10 and 12 make it easier for the injected material to pass through and to fill the bodies 46, 48 with said material.

The open ends of the tubes 10 and 12 are thus completely embedded in the sealant.

The cartridge of the invention is used as follows:

The cartridge is mounted in sealed manner inside the tube or cylindrical housing 30 of FIG. 2 by being pushed in until the enlarged head 28 of the top endpiece 14 comes to press against the top end of the tube or cylindrical housing 30. A hollow injection needle can then be inserted into the blind bore 24 of each endpiece, piercing the material of the endpiece so as to cause the end of the needle to open out into the inside of the filter tube 12. To avoid damaging the filter tube or the dialysis tube, a needle is used which has a closed and rounded end, together with lateral injection orifices.

The needle mounted in the top endpiece 14 may be connected to various receptacles containing, in particular, a cell sample, substances for lysing the cells and cell nuclei, substances for degrading proteins, and rinsing substances. These substances can be inserted into the filter tube 12 by putting the receptacles under pressure or by connecting the needle of the bottom endpiece 16 to a source of suction.

The filter tube 12 and the dialysis tube 10 can be completely drained or emptied by closing the needle of the top endpiece or by withdrawing said needle, given that the material of the body 46 is self-sealing, and by connecting the needle of the bottom endpiece to a source of suction, thereby completely flattening the filter tube 12 and the dialysis tube 10 onto themselves, leaving no residual volume inside said tubes.

The holes or orifices 40 formed in the filter tube 12 immediately beneath the sealing weld line 20 enable substances contained between the filter tubes 12 and the dialysis tube 10 to be discharged by means of the needle of the bottom endpiece 16.

Figure 7:
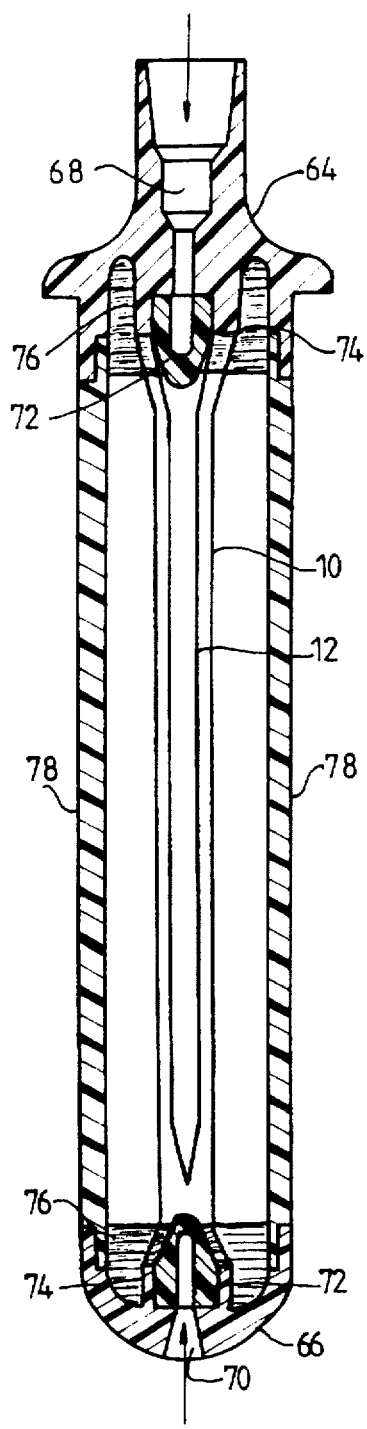
FIG. 7 is a diagram in section of another embodiment of the cartridge.

FIG. 7 is an axial section through a preferred embodiment of the invention, which differs from the above embodiment in that the open top ends of the dialysis tube 10 and of the filter tube 12 are mounted on a top endpiece 64 by means of adhesive while the open bottom end of the dialysis tube 10 is mounted on the bottom endpiece 66 by adhesive, with the filter tube 12 being shorter than the dialysis tube 10 and being closed at its bottom end, e.g. by a transverse weld line, so as to be suspended from its top end inside the dialysis tube 10.

The endpieces 64 and 66 are molded out of plastics material or elastomer, and each has a respective axial passage 68, 70 for receiving an injection or suction needle, with the end of the passage 68, 70 that opens out to the inside of the dialysis tube 10 being closed by a cap 72 made of self-sealant and, for example, engaged in a countersink formed at the end of the passage 68 or 70 in a chimney 74 that projects axially from the inside face of the corresponding endpiece 64 or 66.

The open top ends of the dialysis tube 10 and of the filter tube 12 are engaged on the cap 72 of the top endpiece 64 and optionally on the chimney 74 carrying the cap 72, and they are embedded in adhesive material 76, e.g. of the polymerizable type, which fills the inside space of the endpiece 64 around the chimney 74.

Similarly, the open bottom end of the dialysis tube 10 is engaged on the cap 72 and on the chimney 74 of the bottom endpiece 66 and it is embedded in identical adhesive material 76 that fills the bottom endpiece 66, at least in part.

The ends of the tubes 10 and 12 mounted on the caps 72 and/or the chimneys 74 are relatively flattened and thus of substantially elliptical cross-section, thereby making it easier for these tubes to be completely flattened when suction is applied thereto.

The endpieces 64 and 66 are rigidly interconnected by uprights 78 analogous to the uprights 18 of the first embodiment, said uprights 78 optionally being constituted by portions of a cylinder so as to facilitate guidance of the cartridge in a tube that is designed to receive it, such as the tube of FIG. 2.

Figure 8:
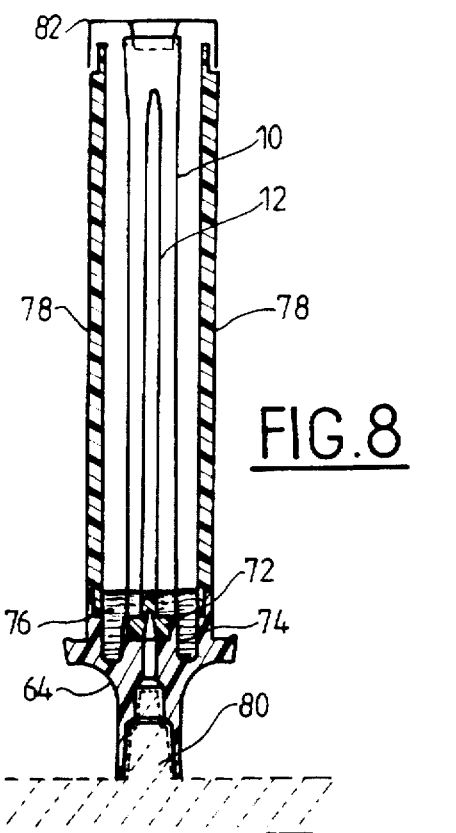
FIGS. 8 and 9 are diagrams showing two steps in the manufacture of the FIG. 7 cartridge.

The cartridge of FIG. 7 is easily manufactured as follows:

Initially, the top endpiece 64 is placed upside-down on a support 80, as shown diagrammatically in FIG. 8, and the corresponding cap 72 is placed in the countersink of the chimney 74, the inside volume of the endpiece 64 around the chimney 74 is then more or less completely filled with adhesive material 76, the filter tube 12 is put into place on the cap 72, the dialysis tube 10 is put into place around the filter tube 12, and its bottom end is engaged on the cap 72 and optionally on the chimney 74, the uprights 78 are put into place on the endpiece 64 with their top ends being held apart by a spreader 82 optionally including a central finger that engages in the open top end of the dialysis tube 10 so as to keep said end open, and the adhesive material 76 is allowed to polymerize or set.

In this way, the cap 72, the ends of the tubes 10 and 12, and the ends of the uprights 78 are all fixed to the endpiece 64.

Figure 9:
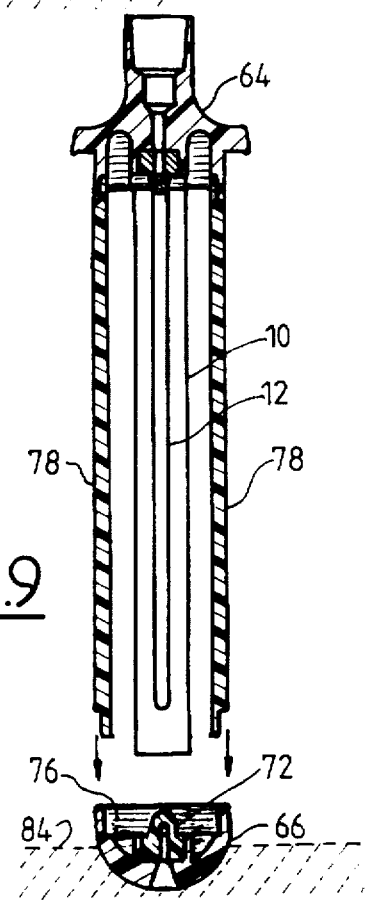

Thereafter, and as shown diagrammatically in FIG. 9, the bottom endpiece 66 is placed on a support 84, the cap 72 is placed in the bottom endpiece 66, the inside volume of the endpiece 66 around the chimney 74 and the cap 72 is filled with adhesive material 76, and the previously prepared assembly is put into place on the bottom endpiece after being turned the other way up and after removing the spreader 82, the bottom end of the dialysis tube 10 engaging on the cap 72 and optionally on the chimney 74 of the bottom endpiece 66, the uprights 78 engaging at their bottom ends on the endpiece 66, and the adhesive material 76 is allowed to set or polymerize, thereby having the effect of fixing the cap 72, the end of the tube 10, and the ends of the uprights 78 on the endpiece 66.

In a variant, the above-described cartridge does not include caps 72. In which case, the passages 68 and 70 open out directly into the flexible tubes 10 and 12 and they are closed by the adhesive material 76 which should then be of the self-sealing type, the ends of the dialysis tube and of the filter tube being engaged on and fixed to the chimneys 74 having the passages 68 and 70 passing therethrough.

The cartridge of FIG. 7 can be used in the same way as the cartridge of the preceding figures, and it has the same advantages, while also being easier to use because the ends of the dialysis tube and of the filter tube are not closed by resilient pinching but are wide open, thereby making it easier to put into place the needles for the purposes of suction and injection of substances.

In general, cartridges of the invention can be used like the cartridge of above-mentioned international application WO 93/01312, with the contents thereof being incorporated herein by reference, and all of the methods described in that international application can be used with the cartridges of the present invention.

Briefly, those methods consist in particular in inserting a sample of cells together with a lysis substance into the filter tube 12 and then in discharging the mixture by suction, with the nuclei of the cells being retained by the tube 12, rinsing is then performed, after which substances for lysing the nuclei and for degrading proteins are injected into the tube 12, dialysis is performed in the tube or housing 30, and DNA is extracted from the dialysis tube 10 by suction.

Advantageously, the simplicity of the structure of cartridges of the invention, and the simplicity with which they can be manufactured makes it possible to produce items that are discardable, and that are used on one occasion only.

I claim:

1. A cartridge for preparing purified nucleic acids, the cartridge comprising:

a dialysis enclosure in the form of a flexible tube, the tube being open at both ends;

a flexible filter tube for retaining cell nuclei, said filter tube being disposed inside the dialysis enclosure, the filter tube being open at one end and closed at the other; and endpieces mounting both ends of the flexible tube of the dialysis enclosure and at least the open end of the filter tube, said endpieces being formed of a material selected from the group consisting of plastics material and elastomers, said endpieces being adapted for insertion of a sample of cells and reaction substances into said filter tube and for discharging reaction substances and purified nucleic acids from said filter tube and said dialysis enclosure.

2. A cartridge according to claim 1, wherein the ends of the filter tube and of the dialysis tube which are mounted in said endpieces are embedded in a sealant.

3. A cartridge according to claim 1, wherein said endpieces include a hollow body or cap of material that is self-sealing after being pierced, said body or cap receiving an open end of the filter tube and/or of the dialysis tube and embedded in a sealant.

4. A cartridge according to claim 1, wherein the filter tube is suspended from its open top end inside the dialysis tube.

5. A cartridge according to claim 1, wherein the ends of the filter tube and of the dialysis tube mounted in said endpieces are relatively flattened and substantially elliptical in shape.

6. A cartridge according to claim 1, wherein said endpieces are rigidly interconnected.

7. A cartridge according to claim 1, wherein the filter tube and the dialysis tube are of substantially the same length and are mounted at their ends in said endpieces, the filter tube being closed in the vicinity of its bottom end by a transverse weld line.

8. A cartridge according to claim 1, wherein said endpieces are interconnected by longitudinal uprights that are fixed to the endpieces by mutual engagement and/or adhesive.

9. A cartridge according to claim 1, wherein said endpieces are mounted in cylindrical rings that are rigidly interconnected by longitudinal uprights.

10. A cartridge according to claim 1, wherein said cartridge is designed to be used in a tube connected to means for circulating a dialysis liquid.

* * * * *